United States Patent [19]
Galliani et al.

[11] Patent Number: 4,927,837
[45] Date of Patent: May 22, 1990

[54] DERIVATIVES OF 3-PIPERIDINE CARBALDEHYDE OXIME AND THEIR USE AS MEDICAMENTS

[75] Inventors: Giulio Galliani; Fernando Barzaghi, both of Monza; Carla Bonetti, Fontanella; Emilio Toja, Milan, all of Italy

[73] Assignee: Roussel Uclaf, Paris, France

[21] Appl. No.: 292,257

[22] Filed: Dec. 30, 1988

[30] Foreign Application Priority Data

Dec. 30, 1987 [IT] Italy .............................. 23280 A/87

[51] Int. Cl.$^5$ .................. A61K 31/445; C07D 211/28
[52] U.S. Cl. ..................................... 514/331; 546/232; 546/246
[58] Field of Search ................ 546/232, 246; 514/331

[56] References Cited

U.S. PATENT DOCUMENTS

| | | | |
|---|---|---|---|
| 3,004,979 | 10/1961 | Druey et al. ......................... | 546/329 |
| 4,408,054 | 10/1983 | Strupczewski et al. ............ | 546/239 |
| 4,710,508 | 12/1987 | Bergmeier et al. ................. | 514/357 |

OTHER PUBLICATIONS

March, "Advanced Organic Chemistry", 3rd Edition (1985), pp. 691-700 and 805-806.

*Primary Examiner*—Robert T. Bond
*Attorney, Agent, or Firm*—Stevens, Davis, Miller & Mosher

[57] ABSTRACT

Derivatives of 3-piperidine carbaldehyde oxime having the formula

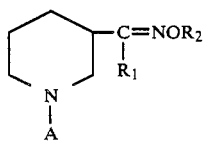

process for preparing the same, therapeutic compositions containing the same, and method of use in treating patients suffering from Alzheimer's disease, senile dementia, or memory disorders in the aged.

15 Claims, No Drawings

DERIVATIVES OF 3-PIPERIDINE CARBALDEHYDE OXIME AND THEIR USE AS MEDICAMENTS

The invention relates to new derivatives of 3-piperidine carbaldehyde oxime, their preparation process and their use as medicaments.

A subject of the invention is compounds of formula (I);

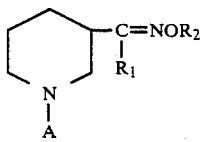

in which $R_1$ represents a hydrogen atom, a linear, branched or cyclic alkyl, alkenyl or alkynyl radical containing up to 8 carbon atoms, $R_2$ represents a hydrogen atom, a linear, branched or cyclic alkyl, alkenyl or alkynyl radical containing up to 8 carbon atoms, a $COalk_1$ radical or $(CH_2)_2 N(alk_2)_2$ radical, $alk_1$ and $alk_2$ representing an alkyl radical containing up to 8 carbon atoms, and A represents a hydrogen atom, a free or esterified hydroxyl radical, a linear, branched or cyclic alkyl, alkenyl or alkynyl radical containing up to 8 carbon atoms, optionally substituted by a free or esterified carboxy radical, or A represents an aralkyl radical containing up to 18 carbon atoms, or A represents a

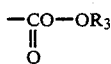

radical in which $R_3$ represents a linear, branched or cyclic alkyl, alkenyl or alkynyl radical containing up to 8 carbon atoms, an aryl radical containing up to 14 carbon atoms, an aralkyl radical containing up to 18 carbon atoms, or an alkylsulphonylalkyl radical containing up to 18 carbon atoms, as well as their addition salts with acids.

Among the addition salts with acids, there can be cited those formed with mineral acids such as hydrochloric, hydrobromic, sulphuric or phosphoric acids, or with organic acids such as the following: formic, acetic, propionic, benzoic, maleic, fumaric, succinic, tartaric, citric, oxalic, glyoxylic or aspartic, alkanesulphonic such as methane- or ethanesulphonic acids, arenesulphonic such as benzene- or paratoluenesulphonic acids.

When $R_1$, $R_2$, $R_3$ or A represents a linear or branched alkyl radical, it is preferred to be one of the following radicals: methyl, ethyl, n-propyl, isopropyl, n-butyl, sec-butyl, isobutyl, n-pentyl, n-hexyl, tert-butyl, tert-pentyl, neopentyl or n-hexyl.

When $R_1$, $R_2$, $R_3$ or A represents an alkenyl or alkynyl radical, it is preferred to be an ethylene radical such as, for example, vinyl, allyl, 1,1-dimethylallyl or 2-butenyl, or an acetylene radical such as, for example, ethynyl or propynyl.

When $R_1$, $R_2$, $R_3$ or A represents a cyclic alkyl radical, it is preferred to be one of the following radicals: cyclopropyl, cyclobutyl, cyclopentyl, cyclohexyl, cyclopropylmethyl, cyclobutylmethyl, cyclopentylmethyl or cyclohexylmethyl.

When A or $R_3$ represents an aralkyl radical, it is preferred to be benzyl or phenethyl.

When A represents an esterified hydroxyl radical, it is preferred to be acetoxy or benzoyloxy.

When A represents an alkyl radical substituted by an esterified carboxy radical, it is preferred to be a radical substituted by an alkoxycarbonyl group in which the alkoxy radical contains up to 8 carbon atoms, such as for example one of the following radicals: methoxy, ethoxy, linear or branched propoxy, or linear or branched butoxy.

$Alk_1$ and $alk_2$ preferably represent methyl, ethyl, n-propyl, isopropyl, n-butyl, sec-butyl or isobutyl.

When $R_3$ represents an aryl radical, it is preferred to be phenyl.

When $R_3$ represents an alkylsulphonylalkyl radical, it is preferred to be the $CH_2SO_2CH_3$, $CH_2CH_2SO_2CH_3$, or $CH_2CH_2CH_2SO_2CH_3$ radical.

Among the preferred compounds of the invention, there can be cited the compounds in which A represents a hydrogen atom, a linear, branched or cyclic alkyl, alkenyl or alkynyl radical, containing up to 8 carbon atoms, or a free or esterified hydroxy radical, as well as their addition salts with organic or mineral acids, and in particular those in which A represents a hydrogen atom, as well as their addition salts with organic or mineral acids, those in which A represents a hydroxy radical, as well as their addition salts with organic or mineral acids, and those in which A represents a benzoyloxy radical, as well as their addition salts with organic or mineral acids.

There can also be cited as preferred compounds of the invention, the compounds in which $R_1$ represents a hydrogen atom, as well as their addition salts with mineral or organic acids.

There can in addition be cited as preferred compounds of the invention, the compounds in which $R_2$ represents a linear or branched alkyl, alkenyl or alkynyl radical containing up to 4 carbon atoms, and in particular those in which $R_2$ represents methyl, as well as their addition salts with organic or mineral acids, and those in which $R_2$ represents propynyl, as well as their addition salts with mineral or organic acids.

Among the compounds of the invention, there can be cited quite particularly the products, the preparation of which is given hereafter in the Examples.

The compounds of the invention show very interesting pharmacological properties and in particular a great cholinomimetic activity, by oral route, which is long-lasting.

It is well known that disorders of learning and of memory in old people are especially linked to a deficiency of the central cholinergic system, in particular in senile dementia and Alzheimer's disease.

It is therefore clear that products which have a central cholinergic action can be used in the therapeutic treatment of these illnesses [Bartus, R.I. Science 217, 408, (1982)].

It has been demonstrated that arecoline, injected by intravenous route, has a positive effect on patients who have a memory deficiency [Sitaram, N., et al, Science 201, 274, (1978)], [Christie, J. E., et al, Brit. J. Psychiatry 138, 46 (1981)].

A limitation to the therapeutic use of arecoline is linked with the fact that this product has a very weak activity by oral route, and a short-lasting period of action.

The products which are the subject of the invention showed, after administration by oral route, a central cholinomimetic activity greater than that of arecoline and a longer-lasting period of action.

A subject of the invention is therefore products of the invention, as medicaments, in particular useful in the treatment of Alzheimer's disease or senile dementia and also in the treatment of memory disorders in the aged.

A subject of the invention is more particularly, as medicaments, the compounds of Examples 2, 6, 7 and 8, as well as their pharmaceutically acceptable salts.

The usual posology varies according to the affection in question, the subject treated and the administration route; it can be between 1 mg and 100 mg/day, preferably from 25 mg to 75 mg/day, and for example between 50 and 75 mg/day in one or several doses for the product of Example 2 administered by oral route.

A subject of the present invention is also pharmaceutical compositions containing as active principle at least one pharmaceutically acceptable product of formula (I). The pharmaceutical compositions of the invention can be solid or liquid and be presented in the pharmaceutical forms currently used in human medicine, such as, for example, plain or sugarcoated tablets, gelules, granules, suppositories, injectable preparations; they are prepared according to the usual methods.

The active principle or principles can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

A subject of the invention is also a process for the preparation of compounds of formula (I) characterized in that the compound of formula (II):

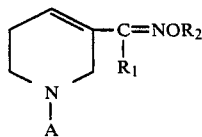
(II)

in which $R_1$, $R_2$ and A have the same significance as defined above, is submitted to the action of a reducing agent, so as to obtain the corresponding compound of formula (I) which, if desired, is submitted to the action of an acid so as to form its salt.

In a preferred method of carrying out the process of the invention, the reducing agent used is hydrogen in the presence of palladium.

Some compounds of formula (II) are known products and are described in European patent application No. 239,445, entitled "New Derivatives of 1,2,5,6-tetrahydropyridin-3-carboxaldehyde oxime, their preparation process, their use as medicaments and the compositions containing them", filed on 24 Feb. 1987.

The products of formula (II) in which A represents a $CO_2R_3$ radical can be prepared by submitting a compound of formula (A):

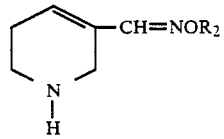
(A)

in which $R_2$ has the same significance as defined above, to the action of an alkoxycarbonylation agent which is able to introduce the $CO_2R_3$ radical, $R_3$ being defined as previously, so as to obtain the corresponding compound of formula (II), which is submitted if desired to the action of an acid so as to form its salt.

In a preferred method of carrying out the above process, the alkoxycarbonylation agent is the compound of formula:

in which X represents a halogen atom.

The compounds of formula (II) in which A represents a $CO_2R_3$ radical can also be prepared according to a process characterized in that a compound of formula (B):

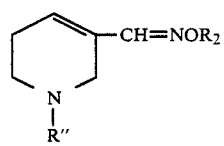
(B)

in which R" represents a linear, branched or cyclic alkyl, alkenyl or alkynyl radical, containing up to 4 carbon atoms, or an aralkyl radical containing up to 14 carbon atoms, is submitted to the action of an agent which can cleave the R" group and introduce the

group, so as to obtain the corresponding compound of formula (II):

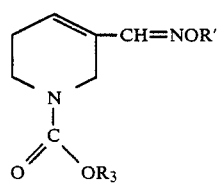
(II)

which is submitted, if desired, to the action of an acid so as to obtain its salt.

In a preferred method of carrying out the process, a compound is used of formula:

X representing a halogen atom, operating hot.

The compounds of formula A and B are described in the European patent application No. 239,445 quoted above.

A subject of the invention is also a variant of the preparation process of compounds of formula (I), characterized in that a compound of formula (III):

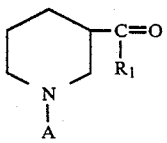 (III)

in which A and $R_1$ have the same significance as defined previously, is submitted to the action of a compound of formula (IV):

 (IV)

or one of its salts, in which $R_2$ has the same significance as defined previously, so as to obtain the corresponding compound of formula (I), which is submitted, if desired, to the action of an acid so as to form its salt.

The products of formula (III) can be prepared for example according to the process described in J. Heterocycl. Chem. 24, 623 (1987).

In a preferred method of carrying out the preparation process, the products of formula (III) and of formula (IV) are used in hydrochloride form.

A subject of the invention is also a preparation process, characterized in that a product of formula (I), when A represents an R″ radical, R″ representing a linear, branched or cyclic alkyl, alkenyl or alkynyl radical, containing up to 4 carbon atoms, or an aralkyl radical containing up to 14 carbon atoms, is submitted to the action of an agent which can cleave the R″ group so as to obtain a compound of formula (I) in which A represents a hydrogen atom, which if desired is salified, or which if desired is submitted either to the action of an alkoxycarbonylation agent which can introduce the $CO_2R_3$ radical, $R_3$ being as defined previously, so as to obtain the corresponding compound of formula (I), which if desired is salified, or submitted to the action of an oxidation agent so as to obtain a compound of formula (I) in which A represents the $OR'_3$ group, in which $R'_3$ represents a protector group of the hydroxy radical, which if desired is salified, or if desired the protector group is eliminated so as to obtain a compound of formula (I) in which A represents a free hydroxy radical, which if desired is salified.

In a preferred method of carrying out the process of the invention,
- the cleavage agent of the R″ group and the alkoxycarbonylation agent are identical to those indicated above for the preparation of products of formula (II),
- the oxidation agent is for example a peroxide such as benzoyl peroxide, or the bis (diphenyl phosphinyl) peroxide,
- the elimination of the protector group of the hydroxy radical is carried out in the usual way. For example, an alkali metal is used such as sodium, in a lower alcohol such as methanol or ethanol or 1N sulfuric acid in the same solvents.

The examples which follow illustrate the invention without however limiting it.

Example 1: 1-methyl-3-piperidine carbaldehyde (O-methyloxime) and its hydrochloride A solution containing 4 g of 1-methyl-1,2,5,6-tetrahydropyridin-3-carbaldehyde O-methyloxime, 60 cm³ of ethyl acetate and 0.4 g of active carbon with 10% of palladium is hydrogenated for 4 hours (volume of hydrogen absorbed 480 cm³). The catalyst is filtered off, a further 0.2 g of active carbon with 10% of palladium is added, and hydrogenation is continued (volume of hydrogen absorbed 90 cm³). After filtering and concentrating under reduced pressure, the residue is chromatographed on silica (eluent: chloroform-methanol 8:2). The solvent is evaporated off and by distillation at 110° C. under 5 mbars, 2 g of product is obtained in the form of a base. The product is dissolved in ether, gaseous hydrochloric acid is introduced and after crystallization from an acetonitrile/ethyl ether mixture 1.95 g of expected hydrochloride is obtained. m.p.=123.5°-124° C.

Analysis: $C_8H_{16}N_2O$, HCl: 192.690
Calculated: C % 49.87 H % 8.89 N % 14.54
Found: 49.84 8.95 14.50

Example 2: 3-piperidine carbaldehyde O-methyloxime and its hydrochloride 4.9 g of (1,2,5,6-tetrahydropyridin-3-carbaldehyde O-methyloxime in solution in 80 cm³ of ethyl acetate is hydrogenated in the presence of 0.5 g of active carbon with 10% of palladium (volume of hydrogen absorbed 800 cm³). The catalyst is filtered off and the solvent is eliminated under reduced pressure. The residue is chromatographed on silica (eluent: chloroform-methanol 7:3) and 3 g of product is obtained in the form of a base, which is salified with hydrochloric acid in ethyl ether. After crystallization from isopropyl alcohol, 1.25 g of expected hydrochloride is obtained. m.p.=158°-160° C.

Analysis: $C_7H_{14}N_2O$, HCl: 178.663
Calculated: C % 47.06 H % 8.46 N % 15.68
Found: 46.96 8.39 15.54

Example 3: 1-ethoxcarbonyl-3-piperidine carbaldehyde (O-methyloxime)

1.5 g of ethyl chloroformate is introduced at 10° C. into a mixture containing 2 g of 3-piperidine carbaldehyde O-methyloxime, 40 cm³ of benzene and 1.42 g of triethylamine. Agitation is maintained for 2 hours at ambient temperature, the benzene phase is washed with diluted hydrochloric acid, dried and concentrated to dryness under reduced pressure. The residue is chromatographed on silica (eluent: toluene-ethyl acetate 8:2) and 0.5 g of expected product is recovered by distillation at 200° C. under 1 mmHg.

Analysis: $C_{10}H_{18}N_2O_3$
Calculated: C % 56.06 H % 8.47 N % 13.08
Found: 56.23 8.39 12.98

Example 4: 1-phenoxycarbonyl-3-piperidine carbaldehyde (O-methyloxime)

The operation is carried out as in Example 3, using 2.2 g of phenyl chloroformate. After chromatography on silica (eluent: toluene-ethyl adetate 9:1) and distillation at 250° C. under 0.08 mmHg, 1.7 g of expected product is recovered. m.p.=40°-41° C.

Analysis: $C_{14}H_{18}N_2O_3$: 262.31
Calculated: C % 64.10 H % 6.92 N % 10.68
Found: 63.96 6.84 10.47

Example 5: 1-methyl-3-piperidin-3-carbaldehyde (O-2-propynyloxime) and its hydrochloride 5 g of [1-methyl-3-piperidine carbaldehyde] prepared as indicated in J. Heterocyclic. Chem. 24 623 (1987), 4.3 g of [O-(2-propynyl)-hydroxylamine] hydrochloride prepared according to U.S. Pat. No. 3,398,180 (1968) and 3.6 g sodium bicarbonate are mixed together in 30 cm$^3$ of water for 2 hours at ambient temperature. Extraction is carried out with ethyl acetate and the extracts are concentrated to dryness. The residue is chromatographed on silica (eluent: chloroform-methanol 5:1) and 5.57 g of product is obtained in the form of a base. 1.5 g of base is taken up in methanol and salified with gaseous hydrochloric acid. After concentrating to dryness, crystallization is carried out from an isopropanol-ethyl ether mixture and 1.67 g of expected hydrochloride is obtained. m.p.=143°-145° C.

Analysis: $C_{10}H_{16}N_2O$, HCl: 216.712
Calculated: C % 55.42 H % 7.91 N % 12.93
Found: 55.31 8.02 13.08

Example 6: 3-piperidine carbaldehyde O-(2-propynyl) oxime and its hydrochloride 4.2 g of alpha-chloroethyl chloroformate is added at −5° C., under inert atmosphere, to a solution of 4 g of [1-methyl-3-piperidine carbaldehyde O-2-propynyl oxime] prepared as in Example 5 in 50 cm$^3$ of dichloroethane. The mixture is taken to reflux for 5 hours, the solvent is eliminated and the residue is taken up in ethyl ether, the insoluble part being filtered off. The filtrate is concentrated to dryness; the residue is taken up in methanol and heated for 30 minutes at reflux. After concentrating to dryness, the residue is chromatographed on silica (eluent: chloroform-methanol 5:1), treated with active carbon, filtered, and the solvents are eliminated. After crystallization from isopropanol and ethyl ether, 1.1 g of expected product is obtained, melting at 139°-141° C. (decomp) and 1.5 g of oily product is obtained.

Analysis: $C_9H_{14}N_2O$, HCl: 202,685
Calculated: C % 53.33 H % 7.46 N % 13.82
Found: 53.80 7.36 13.61

Example 7: 1-benzoyloxy-3-piperidine carbaldehyde (O-methyloxime)

4 g of 3-piperidine carbaldehyde O-methyloxime hydrochloride prepared as in Example 2 and 5.35 g of potassium carbonate are added to 6.8 g of an 80% solution of benzoyl peroxide in 50 cm$^3$ of chloroform. After 16 hours of agitation at ambient temperature, and filtering, the solvent is evaporated off and purified by chromatography on silica (eluent: cyclohexane-ethyl acetate 8:2). 4.3 g of oily product is obtained which solidifies during cooling. m.p.=38°-40° C.

Analysis: $C_{14}H_{18}N_2O_3$: 262,31
Calculated: C % 64.10 H % 6.92 N % 10.68
Found: 63.94 7.03 10.75

Example 8: 1-hydroxy-3-piperidine carbaldehyde (O-methyloxime) and its acid oxalate 2.5 g of 1-benzoyloxy-3-piperidine carbaldehyde (O-methyloxime) prepared as in Example 7 in 95 cm$^3$ of ethyl ether is added to 0.305 g of sodium in solution in 66 cm$^3$ of methanol. After agitation for one hour at ambient temperature, the solvents are evaporated off; the residue is taken up in dilute hydrochloric acid and extracted with ether; the acid phase is alkalized by the addition of sodium bicarbonate, then extracted with ethyl acetate, and the solvent is dried and evaporated. Purification is carried out by chromatography on silica (eluent: ethyl acetate). 1.35 g of product is obtained in the form of a base. An alcohol solution containing 1.163 g of dihydrated oxalic acid is added to 1.45 g of base obtained as above. The solvent is evaporated off, the residue is crystallized from isopropanol and 2.15 g of expected acid oxalate is obtained. m.p.=130°-132° C.

Analysis: $C_7H_{13}N_2O_2$ $(COOH)_2$
Calculated: C % 43.72 H % 6.12 N % 11.33
Found: 43.79 6.28 11.37

Examples of pharmaceutical compositions:

(a) Tablets were prepared according to the following formula:

| Product of Example 1 | 50 mg |
|---|---|
| Excipient q.s. for a tablet completed at | 300 mg |

(detail of excipient: lactose, wheat starch, treated starch, rice starch, magnesium stearate, talc.)

(b) Gelules were prepared according to the following formula:

| Product of Example 1 | 60 mg |
|---|---|
| Excipient q.s. for a gelule completed at | 300 mg |

(detail of excipient: talc, magnesium stearate, aerosil.)

PHARMACOLOGICAL STUDY

Acute Toxicity

The test is carried out on male mice ($CD_1$ Charles Rivers) of 22 to 24 g, which have gone without food for 16 hours. The products are administered by oral route at a dose of 1000, 500, 250, 125 and 62 mg/kg. The mortality was noted for 7 days following the treatment.

| Example | $LD_{50}$ mg/kg |
|---|---|
| 2 | 125 |
| 6 | 100 |
| 7 | >500 |
| 8 | 200 |
| Arecoline | 600 |

Test on the isolated ileum of guinea pigs

Fragments of the ileum of guinea pigs killed by decapitation are removed. The isolated ileum is placed in 10 cm$^3$ of Tyrode's solution at 37° C. and aerated by a mixture of oxygen (95%) and carbon dioxide gas (5%). The contractions due to the products are recorded with a detector linked to a polygraph. The products under test are added at concentrations between $1.10^{-4}M$ and $1.10^{-8}M/1$.

The products showing a contracting effect are tested vis a vis atropine and hexamethonium in order to establish whether the activity is of "muscarine" or "nicotine" type.

The possible antagonistic activity of the products is tested vis a vis acetylcholine.

The agonistic activity is expressed in $pD_2$ (negative logarithm of the dose which produces 50% of the maximum effect.)

| Example | pD$_2$ |
|---|---|
| 2 | 6.05 |
| 6 | 5.35 |
| 7 | <4 |
| 8 | 4.95 |
| Arecoline | 6.90 |

Diarrheic activity

The test is carried out on male mice (CD$_1$ Charles Rivers) weighing 25 to 30 g, which have gone without food for 6 hours. The product, dissolved at 5% in methocel, is administered by oral route, using a probang.

The control animals receive only the excipient.

After treatment, the animals are put separately into cages, the bottoms of which are covered with blotting paper, and are put under observation for 30, 60, 120 and 180 minutes.

The absorbent sheets of paper are changed after each observation.

The consistency of the faeces is evaluated according to the Randall and Baruth method (Arch. Int. Pharmacodyn. 220, 94, 1976), according to the scale of the following values:

0: firm consistency,
1: slightly moist faeces with or without halo of humidity,
2: slightly moist faeces with presence of well-defined circle of humidity,
3: moist faeces with presence of a large circle of humidity,
4: faeces without consistency with presence of a very large circle of humidity.

For each product, the dose which causes diarrhea in 50% of the animals is noted according to the method of Miller and Tainter (Proc. Soc. Exp. Biol. Med., 57, 261, 1944).

| Example | DE$_{50}$ mg/kg |
|---|---|
| 2 | 3.0 |
| 6 | 12 |
| 7 | 10 |
| 8 | 4 |
| Arecoline | 35 |

Hypothermic activity

The test is carried out on male mice (CD$_1$ Charles Rivers) weighing 25 to 30 g, which have gone without food for 6 hours.

The body temperature is noted using a thermocouple placed about 1.5 cm inside the rectum, and connected to an electric temperature recorder.

The products are administered by oral or subcutaneous route and the temperatures are noted at instant 0 and at 30 minutes, 1 hour, 2 hours and 2½ hours after treatment.

The degree of hypothermia is evaluated as the difference between the treated animals and the control animals, and the dose necessary for reducing the body temperature by 1° C. is determined.

| Example | Effective dose O. R. | (−1° C.) in mg/kg SC. R. |
|---|---|---|
| 2 | 1.2 | 1.2 |
| 6 | 7 | 7 |
| 7 | 4 | 4 |
| 8 | 2.0 | 1.6 |
| Arecoline | 194 | 3.0 |

Variation in body temperature

The duration of action of the products is determined using doses capable of reducing the temperature by 1° to 1.5° C.

| | | | VARIATIONS IN BODY TEMPERATURE (°C.) | | | |
|---|---|---|---|---|---|---|
| | Dose | Admin- | Treatment Time in Minutes | | | |
| Example | mg/kg | istration | 0 | 30 | 60 | 120 | 180 |
| 2 | 2 | os | +0.1 | −1.7** | −1.4** | +0.1 | +0.1 |
| | 2 | sc | ±0 | −1.7** | −1.5** | ±0 | +0.1 |
| 6 | 12.5 | os | +0.1 | −1.2** | −1.4** | −0.1 | +0.1 |
| | 12.5 | sc | −0.1 | −1.6** | −1.5** | −0.2 | +0.1 |
| 7 | 5 | os | +0.1 | −1.2** | −1.0** | +0.1 | +0.1 |
| | 5 | sc | +0.1 | −1.2** | −1.1** | ±0 | +0.1 |
| 8 | 2.5 | os | +0.1 | −1.2** | −1.0** | ±0 | +0.2 |
| | 2 | sc | +0.1 | −1.2** | −1.0** | ±0 | ±0 |
| Arecoline, HBr | 3.5 | sc | −0.1 | −1.5** | −0.1 | +0.2 | +0.2 |

**p < 0.01

What is claimed is:

1. A compound of formula (I):

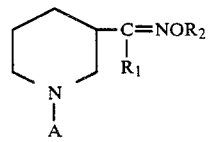

in which R$_1$ represents hydrogen, a linear, branched or cyclic alkyl, alkenyl or alkynyl radical, each containing up to 8 carbon atoms, R$_2$ represents hydrogen, a linear, branched or cyclic alkyl, alkenyl or alkynyl radical, each containing up to 8 carbon atoms, a COalk$_1$ radical or (CH$_2$)$_2$ N(alk$_2$)$_2$ radical, alk$_1$ and alk$_2$ representing an alkyl radical containing up to 8 carbon atoms, and A represents hydrogen, hydroxy, acetoxy or benzoyloxy, a linear, branched or cyclic alkyl, alkenyl or alkynyl radical, each containing up to 8 carbon atoms, optionally substituted by a carboxy radical or an alkoxy carbonyl group in which the alkoxy radical contains up to 8 carbon atoms, A represents benzyl, or A represents

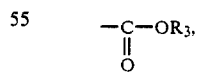

in which R$_3$ represents a linear, branched or cyclic alkyl, alkenyl or alkynyl radical, each containing up to 8 carbon atoms, phenyl, benzyl, or an alkylsulphonylalkyl radical containing up to 18 carbon atoms, as well as its pharmaceutically acceptable addition salts with acids.

2. A compound of formula (I) as defined in claim 1 in which A represents a hydrogen atom, a linear, branched or cyclic alkyl, alkenyl or alkynyl radical, each containing up to 8 carbon atoms, or hydroxy acetoxy or benzoyloxy, as well as its pharmaceutically acceptable addition salts with organic or mineral acids.

3. A compound of formula (I) as defined in claim 2, in which A represents hydrogen, as well as its pharmaceutically acceptable addition salts with organic or mineral acids.

4. A compound of formula (I) as defined in claim 2, in which A represents hydroxy, as well as its pharmaceutically acceptable addition salts with organic or mineral acids.

5. A compound of formula (I) as defined in claim 2, in which A represents a benzoyloxy radical, as well as its pharmaceutically acceptable addition salts with organic or mineral acids.

6. A compound of formula (I) as defined in any one of claims 1 to 5, in which $R_1$ represents hydrogen, as well as its pharmaceutically acceptable addition salts with organic or mineral acids.

7. A compound of formula (I) as defined in any one of claims 1 to 5, characterized in that $R_2$ represents a linear or branched alkyl, alkenyl or alkynyl radical, each containing up to 4 carbon atoms, as well as its pharmaceutically acceptable addition salts with organic or mineral acids.

8. A compound of formula (I) as defined in claim 6, characterized in that $R_2$ represents a linear or branched alkyl, alkenyl or alkynyl radical, each containing up to 4 carbon atoms, as well as its pharmaceutically acceptable addition salts with organic or mineral acids.

9. A compound of formula (I) as defined in claim 7, in which $R_2$ represents a methyl radical, as well as its pharmaceutically acceptable addition salts with organic or mineral acids.

10. A compound of formula (I) as defined in claim 7, in which $R_2$ represents a propynyl radical, as well as its pharmaceutically acceptable addition salts with organic or mineral acids.

11. A compound of formula (I) as defined in claim 8, in which $R_2$ represents a methyl radical, as well as its pharmaceutically acceptable addition salts with organic or mineral acids.

12. A compound of formula (I) as defined in claim 8, in which $R_2$ represents a propynyl radical, as well as its pharmaceutically acceptable addition salts with organic or mineral acids.

13. A compound as defined in claim 1, selected from the group consisting of 3-piperidine carbaldehyde (O-methyloxime), 3-piperidine carbaldehyde O-(2-propynyl) oxime, 1-benzoyloxy-3-piperidine carbaldehyde (O-methyloxime), and 1-hydroxy-3-piperidine carbaldehyde (O-methyloxime), as well as its pharmaceutically acceptable addition salts with organic and mineral acids.

14. A therapeutic composition for the treatment of Alzheimer's disease, senile dementia, or memory disorders in the aged, comprising a cholinomimetically effective amount of a compound as defined in any one of claims 1 to 5 and 8 to 13, and a pharmaceutically acceptable carrier.

15. A method of treating a patient suffering from Alzheimer's disease, senile dementia, or memory loss in the aged, comprising administering to the patient a cholinomimetically effective amount of a compound as defined in any one of claims 1 to 5 and 8 to 13.

* * * * *